United States Patent

Yamamoto

[11] Patent Number: 5,447,507
[45] Date of Patent: Sep. 5, 1995

[54] SANITARY NAPKINS

[75] Inventor: Masamitsu Yamamoto, Kawanoe, Japan

[73] Assignee: Uni-Charm Co., Ltd., Ehime, Japan

[21] Appl. No.: 222,304

[22] Filed: Apr. 4, 1994

Related U.S. Application Data

[63] Continuation of Ser. No. 16,159, Feb. 9, 1993, abandoned.

[30] Foreign Application Priority Data

Feb. 18, 1992 [JP] Japan .................... 4-68981

[51] Int. Cl.⁶ .......................................... A61F 13/15
[52] U.S. Cl. ............................ 604/385.2; 604/386; 604/387
[58] Field of Search ..................... 604/385.1–387, 604/389–390, 395

[56] References Cited

U.S. PATENT DOCUMENTS

| | | |
|---|---|---|
| 4,425,130 | 1/1984 | DesMarais . |
| 4,496,359 | 1/1985 | Pigneul . |
| 4,608,047 | 8/1986 | Mattingly . |
| 4,704,116 | 11/1987 | Enloe . |
| 4,790,838 | 12/1988 | Pigneul et al. . |
| 4,822,435 | 4/1989 | Igaue et al. . |
| 4,911,701 | 3/1990 | Mavinkurve . |
| 4,940,462 | 7/1990 | Salerno . |
| 5,019,070 | 5/1991 | Ruben . |
| 5,032,121 | 7/1991 | Mokry . |
| 5,167,653 | 12/1992 | Igaue et al. . |
| 5,176,669 | 1/1993 | Klemp . |
| 5,234,422 | 8/1993 | Sneller et al. . |
| 5,236,428 | 8/1993 | Zajaczkowski . |
| 5,246,431 | 9/1993 | Minetola et al. . |
| 5,246,432 | 9/1993 | Suzuki et al. . |

FOREIGN PATENT DOCUMENTS

| | | |
|---|---|---|
| 268858A2 | 6/1988 | European Pat. Off. . |
| 0534488 | 3/1993 | European Pat. Off. . |
| 3198851 | 8/1991 | Japan . |
| 3218752 | 9/1991 | Japan . |
| 4009153 | 1/1992 | Japan . |
| 4325153 | 11/1992 | Japan . |
| 2214085 | 8/1989 | United Kingdom . |
| 2243283 | 10/1991 | United Kingdom . |
| 92/07536A1 | 5/1992 | WIPO . |
| 93/04651 | 3/1993 | WIPO . |

*Primary Examiner*—Randall L. Green
*Assistant Examiner*—K. M. Reichle
*Attorney, Agent, or Firm*—Lowe, Price, LeBlanc & Becker

[57] ABSTRACT

An improved sanitary napkin comprising liquid barriers extending along laterally opposite sides of a napkin and provided with elastic members and wings extending outwardly from the liquid barriers, wherein the liquid barriers and the wings are branched from each other so that the liquid barriers are not pulled outward even when the wings are folded back onto the outer surface of a crotch zone of the user's underwear in order to fix the napkin thereto.

12 Claims, 2 Drawing Sheets

SANITARY NAPKINS

This is a continuation of application Ser. No. 08/016,159, filed Feb. 9, 1993 now abandoned, and the benefits of 35 USC 120 are claimed relative to it.

BACKGROUND OF THE INVENTION

This invention relates to sanitary napkins (or sanitary pads) used to absorb and hold menstrual discharges and more particularly to such sanitary napkins provided with wings and liquid barriers adapted to be folded back around a crotch zone of the user's shorts in order to fix the napkin thereto.

Conventional sanitary napkins classified herein for the purpose of explanation as napkins of a first type comprise a liquid-permeable topsheet, a liquid-impermeable backsheet, a liquid-absorbent core sandwiched therebetween, and wings formed by sections of the top- and backsheets which outwardly extend from laterally opposite side edges of the liquid-absorbent core at a longitudinally middle portion of the liquid-absorbent core. In actual use of napkins of this type, the wings are folded back onto the outer surface of a crotch zone of the user's shorts and thereby the wings are fixed thereto with adhesive applied to rear sides of the respective wings. Thus, the napkins are advantageous in that they can be reliably fixed to the crotch zone.

Well known sanitary napkins classified as napkins of a second type include liquid barriers longitudinally extending along laterally opposite sides and adapted to be raised under the effect of elastic elements associated with the respective liquid barriers. Napkins of this type are advantageous in that the liquid barriers effectively contribute to prevent body fluids from laterally leaking.

Sanitary napkins of prior art classified as napkins of a third type comprise an upper napkin and a lower napkin dimensioned wider than the upper napkin so that the former is fixed to the latter at longitudinally opposite ends of the latter. In using napkins of this type, the lower napkin is fixed to a crotch zone of the user's shorts with adhesive applied on a rear side of the lower napkin. Thus, such composite napkins are advantageous in that the upper napkin is free from any adverse influence of deformation possibly occurring in the crotch zone of the user's shorts.

However, the napkins of the first and third types are inferior to the napkins of the second type with respect to the preventive effect against lateral leakage of body fluids because both the napkins of the first type and the napkins of the third type have no liquid barriers characterizing the napkins of the second type. The napkins of the second type are, in turn, inferior to the napkins of the first type as far as fixation of the napkin to a crotch zone of the user's shorts is concerned. In view of this, we attempted to obtain sanitary napkins having combined advantageous features of these first and second types and found that the advantageous feature of the second type can not satisfactorily function when these two advantageous features are merely combined with one another.

More specifically, with such composite napkins of the prior art, the liquid barriers provided on the component napkin of the second type are pulled outward against the contractile force of the associated elastic members as the wings provided on the component napkin of the first type are fixed to the user's shorts by folding the wings back onto an outer side of the crotch zone thereof, with the disadvantageous consequence that the liquid barriers can not satisfactorily operate.

In view of these problems remaining unsolved in spite of various efforts which have been attempted by the prior art, it is a principal object of the invention to provide improved sanitary napkins maintaining the advantages expected from combination of the above-mentioned first, second and third types without loss of the respective advantages.

SUMMARY OF THE INVENTION

The object set forth above is achieved, according to a first embodiment, by a sanitary napkin composed of a liquid-permeable topsheet, a liquid-impermeable backsheet, a liquid-absorbent core sandwiched between these sheets, and wings outwardly extending from laterally opposite sides of the liquid-absorbent core substantially at a longitudinally middle portion of the liquid-absorbent core and applied with adhesive at least on rear sides of the wings, the sanitary napkin comprising liquid barriers longitudinally extending adjacent roots of the wings, and at least free upper ends of the liquid barriers and portions of the wings adjacent the respective roots are constructed so as to be branched from each other so that the free upper ends may be free from a direct influence of outwardly pulling force generated by the respective wings when these wings are folded back.

The object set forth above is also achieved, according to a second embodiment, by a sanitary napkin composed of an upper napkin including a liquid-absorbent core covered with at least a liquid-permeable topsheet and a relatively wide lower napkin including a liquid-impermeable backsheet on a top surface of which a liquid-permeable sheet is bonded at least along opposite side edges of the backsheet so that the upper napkin is bonded to the lower napkin at longitudinally opposite ends of the lower napkin, wherein the upper napkin further including along laterally opposite sides liquid barriers extending longitudinally of the upper napkin and provided with elastic members, respectively, adapted to assist these liquid barriers to be held up and the lower napkin further including wings outwardly extending from laterally opposite side edges substantially at a longitudinally middle portion of the lower napkin and applied with adhesive at least on the bottom surfaces of the respective wings.

For implementation of both the first and second embodiments, it is preferred to form the wings at least from top- and backsheets bonded together and to provide the inner side edges of said topsheets with respective elastic members assisting the inner side edges to be held up. For implementation of the second embodiment, on the other hand, it is preferred to sandwich a liquid-absorbent core between the top- and backsheets of the lower napkin.

BRIEF DESCRIPTION OF THE DRAWINGS

The invention will be described more in detail with reference to the attached drawings, in which.

PREFERRED EMBODIMENTS OF THE INVENTION

Figure 1:
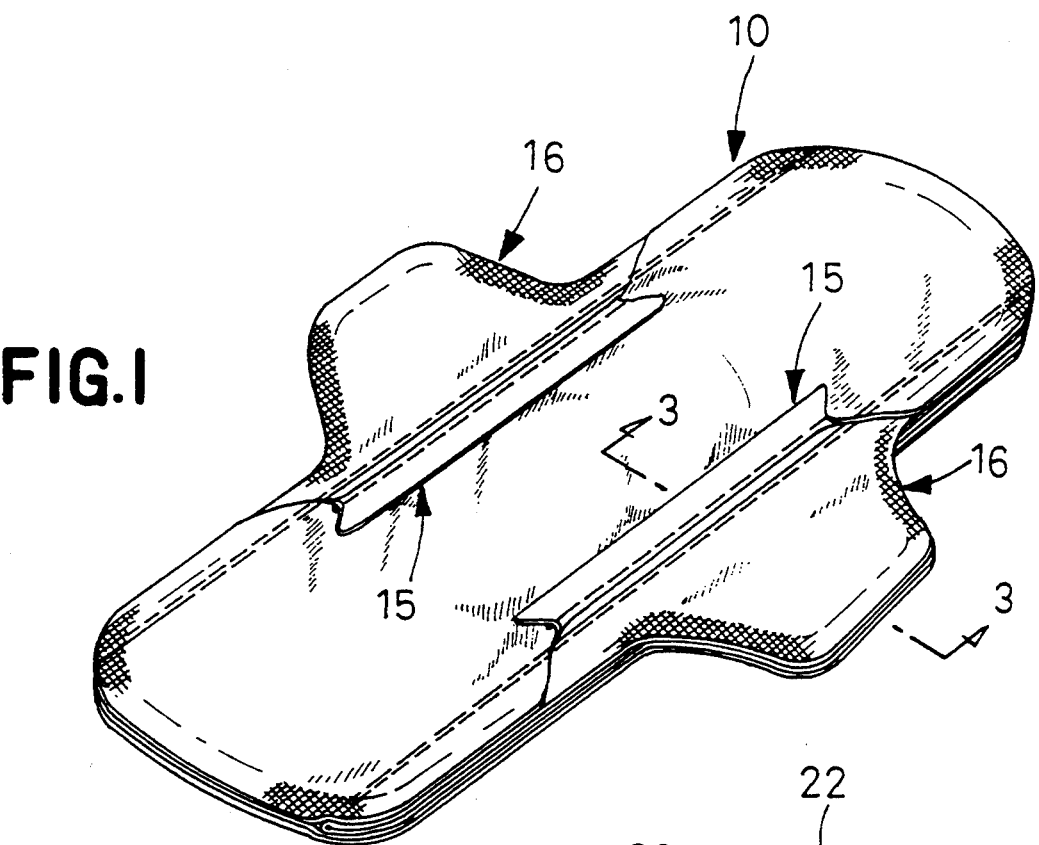
FIG. 1 is a perspective top view showing an embodiment of a sanitary napkin constructed according to the teachings of the invention.
Figure 2:
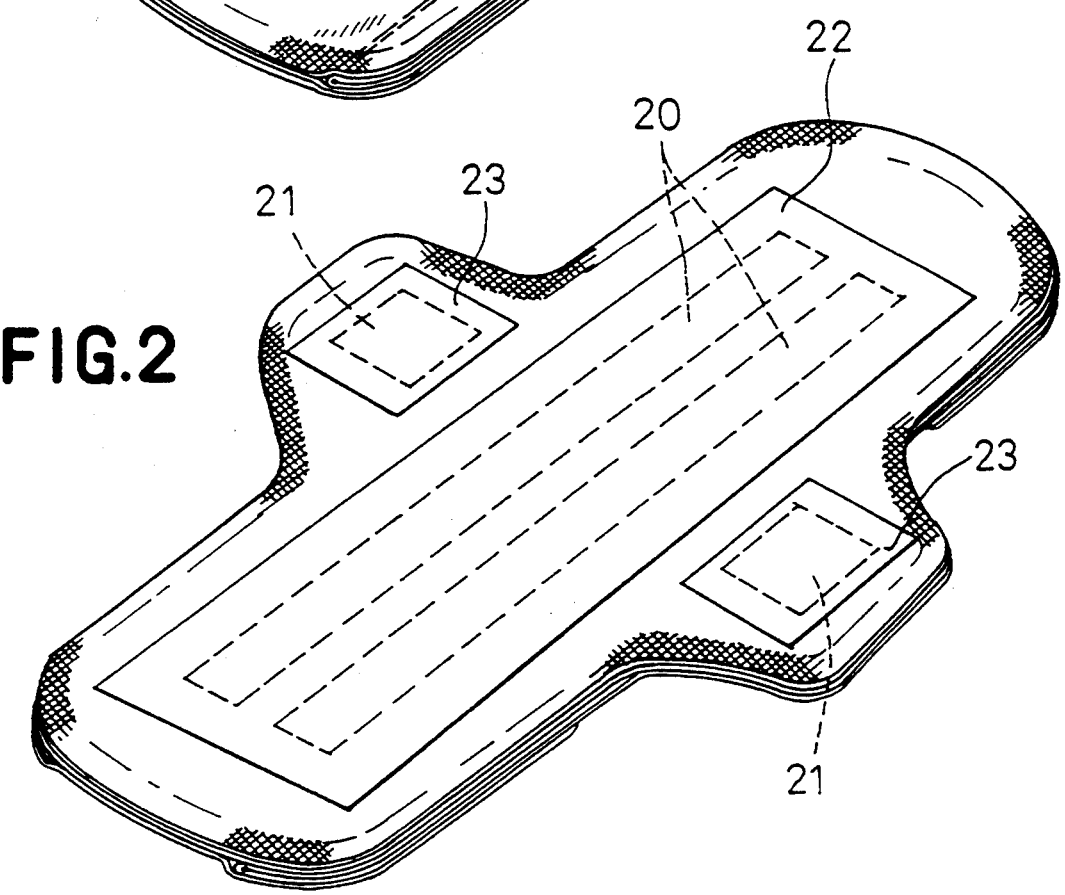
FIG. 2 is a perspective bottom view showing the sanitary napkin.
Figure 3:
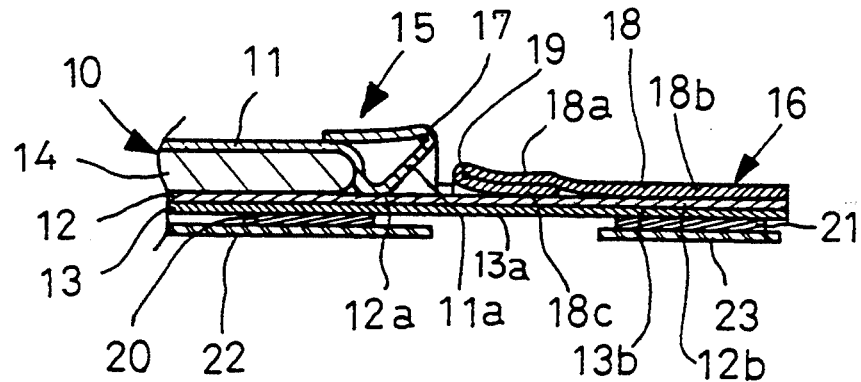
FIG. 3 is a sectional view, in an enlarged scale, taken along a line 3—3 in FIG. 1.

Referring to FIGS. 1 through 3, a napkin 10 basically comprises a liquid-permeable topsheet 11, a liquid-impermeable first backsheet 12, a liquid-impermeable second backsheet 13 underlying and bonded to the first backsheet 12, and a liquid-absorbent core 14 which is smaller than the above-mentioned sheets both in length and width and sandwiched between the topsheet 11 and the first backsheet 12 so that the sheets partially extend beyond the absorbent core 14 in the form of extensions 11a, 12a, 13a. The absorbent core 14 is provided along laterally opposite sides with liquid barriers 15 and wings 16 which outwardly extend from the respective liquid barriers 15. It is also possible without departure from the scope of the invention to employ a first backsheet 12 which is liquid-permeable.

Each liquid barrier 15 is formed by successive steps of folding a first outer extension 11a substantially along a longitudinally middle length thereof up- and inward, bonding an inner edge of this fold above the top of the absorbent core 14 so as to form a sleeve, placing an elastic member 17, as it is stretched, longitudinally inside an outer edge of said sleeve and fixing the elastic member 17 to said sleeve at least at longitudinally opposite ends thereof.

Each wing 16 comprises second outer extensions 12b, 13b extending further outward beyond the outer extensions 12a, 13a at a location adjacent the front end of the napkin 10 and a liquid barrier sheet 18 which comprises, in turn, an inner section 18a bonded to the top of the outer extension 12a, an outer extension 18b being identical to the second outer extensions 12b, 13b in a size as well as in configuration and bonded to the top of second outer extension 12b, and downwardly folded back section 18c being continuous with the inner section 18a. An elastic member 19 is placed, as it is stretched, inside an inner edge of a sleeve formed by said folded back inner section 18c longitudinally of said sleeve and fixed to said sleeve at least at longitudinally opposite ends of the elastic member 19.

If it is desired to provide the liquid barrier 15 with liquid-impermeability, the liquid barrier 15 may be subjected to a suitable water repelling treatment, or the width of the first backsheet 12 may be dimensioned to be substantially equal to a width of the topsheet 11 and outer edges of these sheets may be formed into the liquid barrier 15, or a separately provided liquid-impermeable sheet may be sandwiched between the absorbent core 14 and the first backsheet 12.

Figure 4:
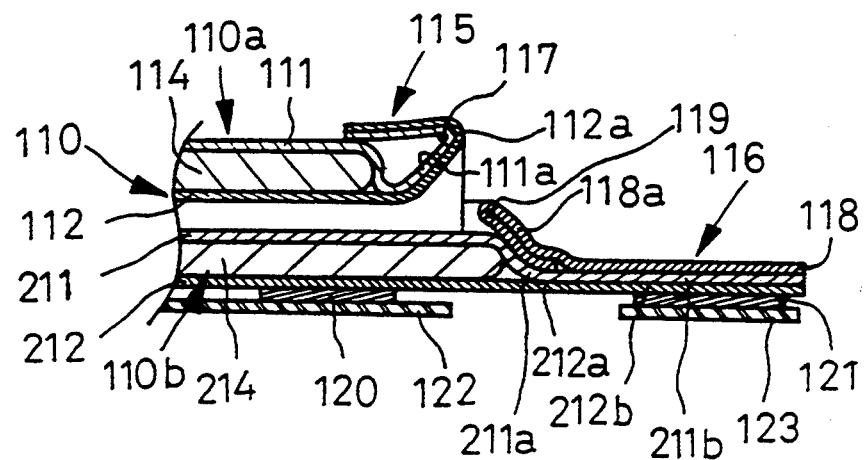
FIG. 4 is a view similar to FIG. 3 showing another embodiment of the sanitary napkin constructed according to the teachings of the invention.

Referring to FIG. 4, another embodiment is shown. A napkin 110 comprises an upper napkin 110a and a lower napkin 110b which is wider than upper napkin 110a. The upper napkin 110a is fixed at longitudinally opposite ends thereof to the top of the lower napkin 110b.

The upper napkin 110a comprises a liquid-permeable topsheet 111, a liquid-impermeable backsheet 112, a liquid-absorbent core 114 which is smaller than the above-mentioned sheets both in length and width and sandwiched therebetween so that these sheets partially extend beyond the absorbent core 114 as respective outer extensions 111a, 112a. The absorbent core 114 is provided along laterally opposite sides with liquid barriers 115. Each liquid barrier 115 is formed by the successive steps of folding the outer extensions 111a, 112a up- and inward, bonding inner edges of these folded portions to the topsheet 111 to form a sleeve, placing an elastic member 117, as it is stretched, longitudinally inside an outer edge of said sleeve and fixing the elastic member 117 to said sleeve at least at longitudinally opposite ends thereof. It is also possible without departure from the scope of the invention to employ a backsheet 112 which is liquid-permeable.

The lower napkin 110b comprises a liquid-permeable topsheet 211, a liquid-impermeable backsheet 212, a liquid-absorbent core 214 which is smaller than the above-mentioned sheets both in length and width and sandwiched between said two sheets, and wings 116 extending outward from laterally opposite sides of the liquid-absorbent core 214, respectively. More specifically, each wing 116 comprises second outer extensions 211b, 212b outwardly extending further beyond respective outer extensions 211a, 212a of said top- and backsheets 211, 212—which, in turn, outwardly extend from each lateral side of the liquid-absorbent core 214, and a liquid-barrier sheet 118. The wing 116 is similar to the previously mentioned wing 16 in a configuration as will be apparent from comparison with FIG. 3 except that an inner section 118a of the liquid barrier sheet 118 which is folded back to define an inner end of the wing 116 and contains therein an elastic member 119 is overlaid on a side edge of the liquid-absorbent core 214 with the topsheet 211 interposed therebetween. An alternative arrangement (not shown) is also possible within the scope of the invention that the lower napkin 110 has no liquid-absorbent core 214.

Referring to FIGS. 3 and 4 (see FIG. 2 also), outer surfaces of the sheets 13, 212 are applied at their central zones with adhesive 20, 120 each in a narrow strip extending in parallel to the longitudinal direction of these sheets 13, 212 while bottom surfaces of the wings 16, 116 are applied at their central zones with adhesive 21, 121 each in a square shape, and these adhesive zones are protected by covering them with release sheets 22, 122 and 23, 123, respectively.

Figure 5:
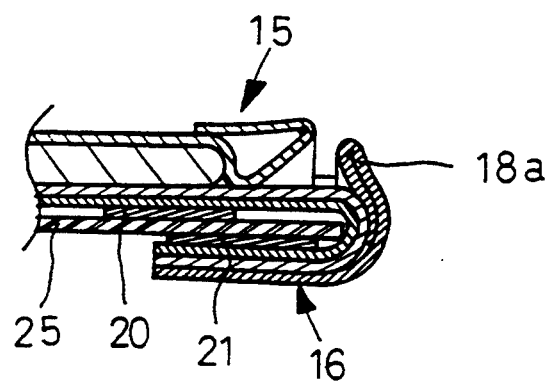
FIG. 5 is a sectional view showing, in an enlarged scale, the sanitary napkin shown by FIG. 3 which has been fixed to a crotch zone of the user's shorts.

Now, the manner in which the napkin 10 constructed as has been mentioned hereinabove is actually used will be described. (No description will be made here in connection with the napkin 110.) The release sheet 22 is removed to expose the adhesive 20 with which the napkin 10 is fixed at its central zone to an inner side of the user's shorts at a central zone 25 thereof (see FIG. 5), then the release sheet 23 is removed to expose the adhesive 21 and the wing 16 is folded back onto an outer side of the crotch zone of the user's shorts so as to fix the wing 16 thereto with said adhesive 21. With the napkin being fixed to the user's shorts in this manner, a free upper end of the liquid barrier 15 and an inner edge of the inner section 18a defining an inner end of the wing 16 are held or raised up under the contractile force of the respective elastic members 17, 19. During such holding up or raising, the liquid barrier 15 is free from any pulling force directed outward due to the folding back of the wing 16. It should be understood here that provision of the elastic member 19 is not essential because the inner edge of the inner section 18a can be held as the wing 16 is folded back even if the elastic member 19 is not provided, i.e., the elastic member 19 serves merely to assist said inner edge to be held.

Respective components of the napkin 10, 110 may be made of the materials used for corresponding components of conventional napkins. For example, the topsheets 11, 111, 211 may be made of nonwoven fabric or porous plastic film, the backsheets 12, 112, 212 may be made of plastic film and the liquid barrier sheets 18, 118 may be made of water repellent nonwoven fabric.

With the sanitary napkin of this invention having the construction and the operation as have been described hereinabove, said liquid barrier is never pulled outward by said wing against the contractile force of the elastic member provided within said liquid barrier but held under the contractile force of this elastic member closely against skin of the user's private parts and thereby satisfactorily prevents body fluid from partially leaking in a lateral direction.

With the embodiment of the sanitary napkin so arranged that the inner edge of the sheet used to constitute the top of said wing normally rises up, this inner edge also contributes to prevent any quantity of body fluids from laterally leaking.

With the embodiment of the sanitary napkin comprising the upper napkin and the lower napkin, the upper napkin can be properly kept in close contact with skin of the user's private parts without adverse influence of deformation such as wrinkles and twists possibly appearing in the lower napkin and/or the crotch zone of the user's shorts, so said lateral leak can be more effectively avoided.

What is claimed is:

1. A sanitary napkin which is adapted to be positioned on a body-facing surface of a crotch portion of an undergarment (25), said napkin (10) comprising
   (a) a liquid-permeable topsheet (11),
   (b) a liquid-impermeable backsheet (13),
   (c) a liquid-absorbent core (14) sandwiched between said sheets, said core (14) having laterally opposite sides,
   (d) two spaced apart wing sections (16) that extend outwardly beyond the laterally opposite sides of said liquid-absorbent core (14) at a longitudinal middle portion of said liquid absorbent core (14),
      (i) each said wing section (16) having an inner portion and an outer portion, said outer portion being adapted to be folded around a side edge of the crotch portion of the undergarment (25),
      (ii) each wing section (16) having front and rear surfaces, the front surface being closest to said crotch portion of the undergarment (25) when the wing section (16) is folded around a side edge of the crotch portion of the undergarment (25),
   (e) a liquid barrier (15) located inwardly of each wing section (16) and adjacent said inner portion of each wing section (16), each liquid barrier (15) having a free upper end which extends upwardly with respect to said backsheet and which is branched with respect to said inner portion of the closest wing section (16) so that each free upper end will not be affected when the wing sections (16) are folded around side edges of the crotch portion of the undergarment, and
   (f) adhesive means on said front surface of each wing section (16) so that each wing section (16) can be adhered to a surface of the undergarment (25) that is opposite the body facing surface of the undergarment (25).

2. A napkin as set forth in claim 1 wherein each wing section (16) comprises said backsheet and an overlying barrier sheet (18) that are bonded together, the side of the barrier sheet (18) that is closest to said core (14) being folded over to form a sleeve which is raised up with respect to the remainder of each wing section (16).

3. A napkin according to claim 2 wherein each sleeve encloses a stretched elastic member (19) which assists in positioning said sleeve in a raised position.

4. A napkin as set forth in claim 1 wherein said liquid barrier (15) comprises a portion of said topsheet (11) that is folded over so as to extend upwardly with respect to said backsheet.

5. A napkin according to claim 1 wherein each liquid barrier (15) encloses a stretched elastic member (17) which assists in positioning the liquid barrier (15) in a raised position.

6. A napkin according to claim 1 which also contains adhesive means on the surface of the backsheet that is farthest away from said core (14) to adhere a portion of an undersurface of the napkin to the body-facing surface of the crotch portion of the undergarment (25).

7. A composite sanitary napkin which is adapted to be positioned on a body facing surface of a crotch portion of an undergarment, said napkin comprising upper and lower liquid-absorbent cores (110a, 110b),
   said upper liquid-absorbent core (110a) being covered with a liquid-permeable topsheet (111) and containing spaced apart liquid barriers (115) that extend upwardly with respect to the lower side of said upper core (110a), the liquid barriers having free upper ends that enclose elastic members (117) which assist in positioning the liquid barriers (115) in a raised position, said upper liquid-absorbent core (110a) having laterally opposite sides,;
   said lower liquid-absorbent core (110b) being wider than said upper liquid-absorbent core (110a), the lower core (110b) having its lower side covered by a liquid-impermeable backsheet (212);
   two spaced apart wing sections (116) that extend outwardly beyond the laterally opposite sides of said upper liquid-absorbent core (110a) at a longitudinal middle portion of said lower liquid absorbent core (110b),
      (i) each said wing section (116) having an inner portion and an outer portion, said outer portion being adapted to be folded around a side edge of the crotch portion of the undergarment (25),
      (ii) each wing section (116) having front and rear surface, the front surface being closest to the crotch portion of the undergarment (25) when the wing section (116) is folded around the side edge of the crotch portion of the undergarment (25), and
   adhesive means on said front surface of each wing section (116) so that each wing section (116) can be adhered to a surface of the undergarment (25) that is opposite the body facing surface of the undergarment (25).

8. A napkin as set forth in claim 7 wherein each wing section (116) comprises said backsheet and an overlying barrier sheet (118) that are bonded together, the side of the barrier sheet (118) that is closest to said lower core (110b) being folded over to form a sleeve which is raised up with respect to the remainder of each wing section (116).

9. A napkin according to claim 8 wherein each sleeve encloses a stretched elastic member (119) which assists in positioning said sleeve in a raised position.

10. A napkin as set forth in claim 7 wherein each liquid barrier (115) comprises a portion of said topsheet (111) that is folded over so as to extend upwardly with respect to said backsheet (212).

11. A napkin as set forth in claim 7 wherein each liquid barrier (115) comprises portions of said topsheet (111) and a backsheet (112) that are bonded together and folded over to extend upwardly with respect to the remaining portion of the backsheet (112).

12. A napkin according to claim 7 which also contains adhesive means on a surface of the backsheet (212) that is farthest away from said lower core (110b) to adhere a portion of an undersurface of the napkin to the body-facing surface of the crotch portion of the undergarment (25).

* * * * *